United States Patent [19]

Ishihara et al.

[11] 4,391,984

[45] Jul. 5, 1983

[54] ALKYNYL HALIDE COMPOUNDS AND ALKENYL ACETATE COMPOUNDS THEREFROM

[75] Inventors: Toshinobu Ishihara; Akira Yamamoto; Kenichi Taguchi, all of Joetsu, Japan

[73] Assignee: Schin-Etsu Chemical Co., Ltd., Tokyo, Japan

[21] Appl. No.: 266,614

[22] Filed: May 22, 1981

[30] Foreign Application Priority Data

May 26, 1980 [JP] Japan .................................. 55-69724
May 29, 1980 [JP] Japan .................................. 55-71740

[51] Int. Cl.³ .................................................. C07C 67/10
[52] U.S. Cl. ...................................... 560/236; 560/237
[58] Field of Search ................................ 560/236, 237

[56] References Cited

PUBLICATIONS

Roberts & Caseno, Basic Principles of Organic Chemistry, pp. 358 and 830 (1965).

Primary Examiner—Paul J. Killos
Attorney, Agent, or Firm—Toren, McGeady and Stanger

[57] ABSTRACT

The invention provides a novel method for the synthetic preparation of an ω-haloalkyne compound of the general formula R—C≡C—(CH$_2$)$_n$X, in which X is a halogen atom, R is a monovalent hydrocarbon group and n is 4, 5 or 6, by the coupling reaction of a Grignard reagent RMgX' and an ω-halo-1-bromoalkyne compound of the formula X—(CH$_2$)$_n$C≡C-Br. The ω-haloalkyne compound obtained in the above can be readily converted to the corresponding alkenyl acetate of the formula R—CH=CH—(CH$_2$)$_n$OCOCH$_3$ by first acetylating and then partially hydrogenating in the presence of a Lindlar catalyst. In particular, 7,11-hexadecadienyl acetate, which is a sexual pheromone compound of a noxious insect, is obtained in the same route of synthesis starting with the Grignard reagent of a 1-halo-3-octene and 1,8-dibromo-1-octyne.

4 Claims, No Drawings

ALKYNYL HALIDE COMPOUNDS AND ALKENYL ACETATE COMPOUNDS THEREFROM

BACKGROUND OF THE INVENTION

The present invention relates to a method for the synthetic preparation of an alkynyl halide compound and further relates to a method for the preparation of an alkenyl acetate compound which can be derived from the alkynyl halide compound as an intermediate. In particular, the invention relates to a method for the preparation of 7,11-hexadecadinyl acetate known as a sexual pheromone compound of pink bolloworm.

As is well known, a specific compound is attractive to a specific species of insects of a sex even with an extremely small amount and such a compound known by the name of a sexual pheromone compound presents a promising means for the extermination of noxious insects in the fields. It is also known that the sexual pheromone compounds of several important noxious insects in the agriculture and forestry chemically belong to a class of alkenyl acetate compounds. For example, the sexual pheromone compound of pink bolloworm is known to be the above mentioned 7,11-hexadecadienyl acetate.

Accordingly, the inventors have conducted to develop a novel and improved method for the synthetic preparation of such alkenyl acetate compounds and arrived at an idea that the desired alkenyl acetate compound may be advantageously prepared from an alkynyl halide compound as an intermediate.

Unfortunately, there have been known no industrially advantageous method for the synthesis of such an alkynyl halide compound or an alkenyl acetate compound such as 7,11-hexadecadienyl acetate to present a great obstacle to the practical application of the sexual pheromone compounds for the extermination of the noxious insects.

SUMMARY OF THE INVENTION

Therefore it is an object of the present invention to provide a novel and improved method for the synthetic preparation of alkynyl halide compounds in general.

A further object of the invention is to provide a novel and improved method for the synthetic preparation of alkenyl acetate compounds starting from the corresponding alkynyl halide compound as an intermediate. In particular, the invention provides an advantageous method for the synthetic preparation of 7,11-hexadecadienyl acetate with 1-bromohexadeca-11-en-7-yne as the intermediate compound.

The method of the present invention for the preparation of an alkynyl halide compound represented by the general formula $R-C \equiv C-(CH_2)_n X$, in which X is a halogen atom, R is a monovalent hydrocarbon group and n is an integer of 4, 5 or 6, comprises reacting a Grignard reagent $RMgX'$, in which R has the same meaning as defined above and $X'$ is a halogen atom which may be the same as or different from X, and an α-halogenoalkynyl-1 bromide of the formula $X-(CH_2)_n C \equiv C-Br$, in which X and n each have the same meaning as defined above. This coupling reaction is advantageously carried out in tetrahydrofuran as a solvent in the presence of a copper halide as a catalyst.

Further, the synthetic preparation of an alkenyl acetate compound from an alkynyl halide is performed by the steps of acetylation of the alkynyl halide compound and then partial hydrogenation of the acetylated compound in the presence of a Lindlar catalyst.

In particular, 7,11-hexadecadienyl acetate expressed by the formula $CH_3(CH_2)_3CH=CH(CH_2)_2CH=CH(CH_2)_6OCOCH_3$ is prepared by first reacting a Grignard reagent of 1-halo-3-octene and 1,8-dibromo-1-octyne to form 1-bromohexadeca-11-en-7-yne which is then acetylated and partially hydrogenated in the presence of a Lindlar catalyst.

DETAILED DESCRIPTION OF THE PREFERRED EMBODIMENTS

In the first place, the method for the preparation of the alkynyl halide compounds $R-C \equiv C-(CH_2)_n X$ is described in detail.

The starting materials in the method are a Grignard reagent of the formula $RMgX'$ and an ω-halo-1-bromoalkyne or ω-halogenoalkynyl-1 bromide compound of the formula $X-(CH_2)_n C \equiv C-Br$, in which the symbols R, X, X' and n each have the same meaning as defined above. The group denoted by R is a monovalent hydrocarbon group such as alkyl groups, e.g. ethyl, propyl and butyl groups, alkenyl groups, e.g. vinyl, cis-3-octenyl and trans-3-octenyl groups, aryl groups, e.g. phenyl group, and alkynyl groups, e.g. propargyl group. The Grignard reagent $RMgX'$ can be readily prepared in a conventional manner from a corresponding halide $RX'$ and metallic magnesium. The halogen atom denoted by $X'$ is preferably a chlorine atom or a bromine atom.

The other reactant to be reacted with the above Grignard reagent is an ω-halo-1-bromoalkyne compound expressed by the general formula given above. In the formula, X is a halogen atom such as a chlorine and a bromine atom, preferably, bromine, and n is a number of 4, 5 or 6. Examples of the ω-halo-1-bromoalkyne compound are: 1,6-dibromohexyne-1,1,7-dibromoheptyne-1 and 1,8-dibromooctyne-1. These ω-halo-1-bromoalkyne compounds can be obtained by the reaction of a corresponding ω-halo-1-alkyne compound $X-(CH_2)_n C \equiv CH$ with potassium hypobromite.

The reaction of the ω-halo-1-bromoalkyne compound and the Grignard reagent is expressed by the following reaction equation:

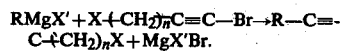

$RMgX' + X-(CH_2)_n C \equiv C-Br \rightarrow R-C \equiv C-(CH_2)_n X + MgX'Br.$ This reaction is carried out by adding a solution of the Grignard reagent in tetrahydrofuran dropwise into the reaction vessel containing the ω-halo-1-bromoalkyne compound, if necessary, diluted with tetrahydrofuran. The molar ratio of the ω-halo-1-bromoalkyne compound to the Grignard reagent is preferably in the range from 1.0 to 1.5 moles of the former per mole of the latter. When the amount of the ω-halo-1-bromoalkyne compound is smaller than above, the yield of undesired by-products may be increased. The reaction temperature is usually in the range from $-20°$ to $+60°$ C. or, preferably, from $-5°$ to $+10°$ C. Lower temperatures are undesirable because of the increased yield of the by-products.

In carrying out the above described coupling reaction between the Grignard reagent and the ω-halo-1-bromoalkyne compound, it is preferable to accelerate the reaction by adding a small amount of a copper halide to the reaction mixture as a catalyst. Suitable copper halide is exemplified by copper (I) chloride, copper (I) bromide and copper (I) iodide.

As is mentioned before, the alkynyl halide compound of the formula R—C≡C-(CH$_2$)$_n$X obtained as described above can be converted to the corresponding alkenyl acetate compound of the formula R—CH=CH-(CH$_2$)$_n$OCOCH$_3$ by the steps of acetylation and partial hydrogenation in the presence of a Lindlar catalyst. The synthetic procedure of the above mentioned acetylation and partial hydrogenation is substantially the same for all of the alkynyl halide compounds irrespective of the kinds of the groups R and X and the number of n so that, in the following, description is given for the preparation of 7,11-hexadecadienyl acetate starting from 1-halo-3-octene and 1,8-dibromo-1-octyne as the most typical case.

One of the starting reactants 1-halo-3-octene is expressed by the formula CH$_3$(CH$_2$)$_3$CH=CH(CH$_2$)$_2$X', in which X' has the same meaning as defined above, is readily obtained by the partial hydrogenation of 3-octyn-1-ol CH$_3$(CH$_2$)$_3$CH≡CH(CH$_2$)$_2$OH into cis-3-octen-1-ol followed by the halogenation of the hydroxy group with a halogenating agent. It is of course that, when the cis-isomer of the 1-halo-3-octene is used as the starting reactant, the resultant 7,11-hexadecadienyl acetate is the so-called Z,Z-isomer while, when the 1-halo-3-octene is a mixture of the cis- and trans-isomers, the resultant 7,11-hexadecadienyl acetate is also a mixture of the corresponding Z,Z- and Z,E-isomers.

The first step of the synthesis is the preparation of the Grignard reagent 3-octenylmagnesium halide from 1-halo-3-octene and metallic magnesium in a conventional manner in tetrahydrofuran as the solvent.

On the other hand, 1,8-dibromo-1-octyne and a copper halide as the catalyst are dissolved in tetrahydrofuran in a reaction vessel to form a reaction mixture, into which the above prepared Grignard reagent in tetrahydrofuran is added dropwise to effect the reaction between the reactants followed by hydrolysis and distillation to give 1-bromohexadeca-11-en-7-yne. The reaction is expressed by the following reaction equation:

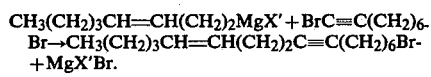
CH$_3$(CH$_2$)$_3$CH=CH(CH$_2$)$_2$MgX'+BrC≡C(CH$_2$)$_6$-Br→CH$_3$(CH$_2$)$_3$CH=CH(CH$_2$)$_2$C≡C(CH$_2$)$_6$Br-+MgX'Br.

The molar ratio of the 1,8-dibromo-1-octyne to the Grignard reagent is usually in the range of 1.0 to 1.5 moles of the former per mole of the latter. When the amount of the former is too small, the amounts of undesirable by-products may increase while an excessive amount thereof is economically disadvantageous.

The reaction is carried out usually at a temperature from −20° to +60° C. or, preferably, from −5° to +10° C. Lower temperatures than above may lead to an increased yield of the by-products.

The copper halide used as the catalyst is preferably a halide of monovalent copper such as copper (I) chloride, copper (I) bromide and copper (I) iodide. The catalyst is used preferably in an amount from 5 to 30 g per mole of the above mentioned Grignard reagent as the reactant.

In the next place, the 1-bromohexadeca-11-en-7-yne obtained in the above described manner is admixed with at least equimolar amount of an alkali metal salt of acetic acid, e.g. sodium or potassium acetate, with dilution with acetic acid and heated with agitation at the refluxing temperature. After completion of the reaction, the reaction mixture is cooled and washed with water and the organic phase is taken and distilled under reduced pressure to give hexadeca-11-en-7-ynyl-1 acetate of the formula CH$_3$(CH$_2$)$_3$CH=CH(CH$_2$)$_2$C≡C(CH$_2$)$_6$OCOCH$_3$.

The yield is usually as high as 95% or more of the theoretical value.

The next step is the partial hydrogenation of the thus obtained acetylenic acetate in the presence of a Lindlar catalyst to give the desired 7,11-hexadecadienyl acetate of the formula CH$_3$(CH$_2$)$_3$CH=CH(CH$_2$)$_2$CH=CH(CH$_2$)$_6$OCOCH$_3$.

The reaction of partial hydrogenation is carried out preferably at a temperature from 20° to 80° C. under pressurization with hydrogen to give a pressure from 1 to 20 atmospheres or, preferably, from 4 to 10 atmospheres. The amount of the Lindlar catalyst to be added to the reaction mixture is preferably from 0.5 to 5.0% by weight based on the amount of the acetylenic acetate compound.

Following are the examples to illustrate the present invention in further detail.

EXAMPLE 1

Into a flask of 500 ml capacity were taken 54 g of 1,8-dibromo-1-octyne, 200 ml of tetrahydrofuran and 1 g of copper (I) bromide to form a reaction mixture and 200 ml of a tetrahydrofuran solution containing the Grignard reagent prepared from 29.4 g of cis-3-octene-1 chloride were added dropwise into the reaction mixture kept at 0° C. with agitation to effect the reaction.

After completion of the reaction, the reaction mixture, following removal of the precipitated salt by filtration and tetrahydrofuran by distillation, was subjected to distillation under reduced pressure to give 47.8 g of cis-11-hexadecen-7-yne-1 bromide of the formula CH$_3$(CH$_2$)$_3$CH=CH(CH$_2$)$_2$C≡C(CH$_2$)$_6$Br. The yield was about 83% of the theoretical value.

EXAMPLE 2

Into a flask of 500 ml capacity were taken 48 g of 1,6-dibromo-1-hexyne, 200 ml of tetrahydrofuran and 1 g of copper (I) bromide to form a reaction mixture and 200 ml of a tetrahydrofuran solution containing 0.2 mole of n-propylmagnesium chloride prepared in advance were added dropwise into the reaction mixture kept at 0° C. with agitation to effect the reaction.

After completion of the reaction, the reaction mixture, following removal of the precipitated salt by filtration and tetrahydrofuran by distillation, was subjected to distillation under reduced pressure to give 16 g of 5-nonyne-1 bromide of the formula CH$_3$(CH$_2$)$_2$C≡C(CH$_2$)$_4$Br. The yield was about 79% of the theoretical value.

EXAMPLE 3

Into a reaction vessel of 200 ml capacity were taken 30 g of the cis-11-hexadecen-7-yne bromide prepared in Example 1 above, 40 g of glacial acetic acid and 30 g of potassium acetate and the reaction mixture was heated for 3 hours at the refluxing-temperature of 164° C. to effect the reaction. After completion of the reaction, 100 ml of water were added to the reaction mixture and the organic solution taken by phase separation was subjected to distillation under reduced pressure to give 22.8 g of cis-11-hexadecen-7-yne-1 acetate. The yield was about 95% of the theoretical value.

Into an autoclave were introduced 22.8 g of the cis-11-hexadecen-7-yne-1 acetate obtained above, 100 ml of pyridine and 1 g of a Lindlar catalyst and the partial hydrogenation of the acetylenic acetate was carried out by pressurizing with hydrogen to a pressure of 10 kg/cm² at 40° C. for 3 hours. After completion of the reaction, the reaction mixture was taken out of the autoclave and distilled under reduced pressure to give 23 g of cis, cis-7,11-hexadecadienyl acetate. This compound was effective as a sexual pheromone of pink bollworm.

What is claimed is:

1. A method for the preparation of an alkenyl acetate having the general formula $$R-CH=CH+CH_2)_nOCOCH_3$$

in which R is a monovalent hydrocarbon group and n is a number of 4, 5 or 6, which comprises the steps of
(a) reacting a Grignard reagent represented by the general formula $$RMgX',$$

in which R has the same meaning as defined above and X' is a halogen atom, and an ω-halo-1-bromoalkyne compound represented by the general formula $$X+CH_2)_nC≡C-Br,$$

in which X and n each have the same meaning as defined above, to form an alkynyl halide compound having the general formula $$R-C≡C+CH_2)_nX,$$

in which R, X and n each have the same meaning as defined above,
(b) acetylating the alkynyl halide compound to form an alkynyl acetate compound having the general formula $$R-C≡C+CH_2)_nOCOCH_3,$$

in which R and n each have the same meaning as defined above, and
(c) partially hydrogenating the alkynyl acetate compound in the presence of a Lindlar catalyst.

2. A method for the preparation of 7,11-hexadecadienyl acetate having the formula $$CH_3(CH_2)_3CH=CH(CH_2)_2CH=CH(CH_2)_6OCOCH_3$$

which comprises the steps of
(a) reacting the Grignard reagent of a 1-halo-3-octene expressed by the formula $$CH_3(CH_2)_3CH=CH(CH_2)_2X',$$

in which X' is a halogen atom, and 1,8-dibromo-1-octyne having the formula $$Br+CH_2)_6C≡C-Br,$$

to form 1-bromohexadeca-11-en-7-yne having the formula $$CH_3(CH_2)_3CH=CH(CH_2)_2C≡C(CH_2)_6Br,$$

(b) acetylating the 1-bromohexadeca-11-en-7-yne to form hexadeca-11-en-7-ynyl acetate having the formula $$CH_3(CH_2)_3CH=CH(CH_2)_2C≡C(CH_2)_6OCOCH_3,$$

and
(c) partially hydrogenating the hexadeca-11-en-7-ynyl acetate in the presence of a Lindlar catalyst.

3. A method for the preparation of an alkenyl acetate having the formula $$R-CH=CH+CH_2)_nOCOCH_3,$$

in which R is a monovalent hydrocarbon group and n is a number of 4, 5 or 6, which comprises the steps of:
(a) reacting from 1.0 to 1.5 moles of the Grignard reagent having the formula $$RMgX',$$

in which X' is a halogen atom, and 1.0 mole of an ω-halo-bromoalkyne compound having the formula $$X+CH_2)_nC≡C-Br,$$

in a tetrahydrofuran solution at a temperature in the range from −5° to +10° C. in the presence of a catalytic amount of a copper halide to form an alkynyl halide compound having the formula $$R-C≡C+CH_2)_nX,$$

(b) acetylating the alkynyl halide compound by reacting it under the heating with an alkali metal acetate as diluted with acetic acid to form an alkynyl acetate compound having the formula $$R-C≡C+CH_2)_nOCOCH_3,$$

and
(c) partially hydrogenating the alkynyl acetate compound in the presence of a Lindlar catalyst at a temperature of 4 to 10 atmospheres.

4. A method for the preparation of 7,11-hexadecadienyl acetate having the formula $$CH_3(CH_2)_3CH=CH(CH_2)_2CH=CH(CH_2)_6OCOCH_3$$

which comprises the steps of
(a) reacting from 1.0 to 1.5 moles of the Grignard reagent of a 1-halo-3-octene expressed by the formula $$CH_3(CH_2)_3CH=CH(CH_2)_2X',$$

in which X' is a halogen atom, and 1,8-dibromo-1-octyne having the formula $$Br+CH_2)_6C≡C-Br,$$

to form 1-bromohexadeca-11-en-7-yne having the formula $$CH_3(CH_2)_3CH=CH(CH_2)_2C≡C(CH_2)_6Br,$$

(b) acetylating the 1-bromohexadeca-11-en-7-yne to form hexadeca-11-en-7-ynyl acetate having the formula $$CH_3(CH_2)_3CH=CH(CH_2)_2C{\equiv}C(CH_2)_6OCOCH_3,$$

and (c) partially hydrogenating the hexadeca-11-en-7-ynyl acetate in the presence of a Lindlar catalyst.

* * * * *